United States Patent [19]

Gordon et al.

[11] Patent Number: 4,669,476
[45] Date of Patent: Jun. 2, 1987

[54] COLD APPLICATION AND COMPRESSIVE BANDAGE

[75] Inventors: Tim H. Gordon, Ridgefield Pk.; Mark Zabrowsky, Hackensack, both of N.J.

[73] Assignee: Becton, Dickinson and Company, Franklin Lakes, N.J.

[21] Appl. No.: 276,428

[22] Filed: Jun. 22, 1981

[51] Int. Cl.[4] ............................................. A61F 7/00
[52] U.S. Cl. ................................................ 128/399
[58] Field of Search ....................... 128/399, 402, 403

[56] References Cited

U.S. PATENT DOCUMENTS

| | | | |
|---|---|---|---|
| 3,149,943 | 9/1964 | Amador | 128/402 |
| 3,736,769 | 6/1973 | Petersen | 128/402 |
| 3,882,867 | 5/1975 | Moran | 128/402 |
| 3,900,035 | 8/1975 | Welch et al. | 128/402 |
| 4,044,773 | 8/1977 | Baldwin | 128/402 |
| 4,055,188 | 10/1977 | Pelton | 128/402 |
| 4,087,150 | 3/1978 | Tyson | 128/402 |
| 4,092,982 | 6/1978 | Salem | 128/402 |
| 4,204,543 | 5/1980 | Henderson | 128/402 |
| 4,243,041 | 1/1981 | Paul | 128/402 |

Primary Examiner—C. Fred Rosenbaum
Assistant Examiner—C. W. Shedd
Attorney, Agent, or Firm—Richard J. Rodrick; John L. Voellmicke

[57] ABSTRACT

A bandage for the simultaneous application of cold therapy and compression comprises an elastic material for wrapping around a portion of a user's body. A refrigeratable pack includes a tab extending therefrom. The refrigeratable pack is removably held on said elastic material during use so that the tab is accessible for grasping by the user.

7 Claims, 7 Drawing Figures

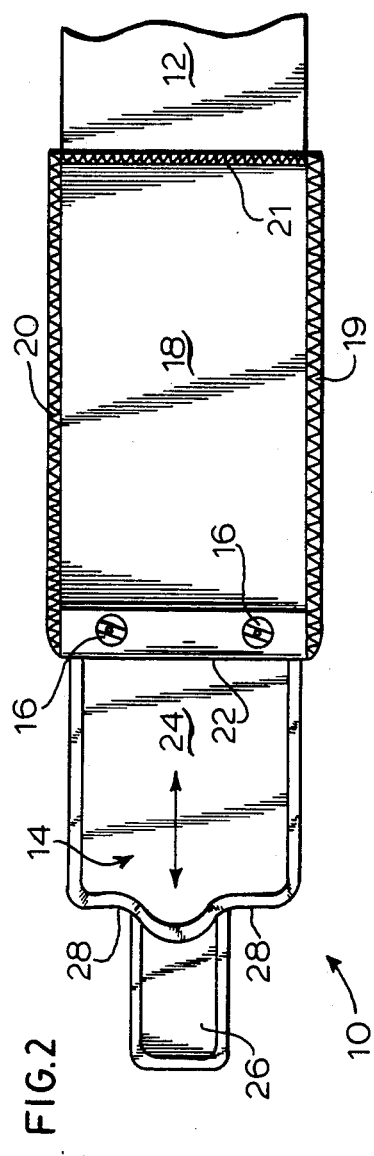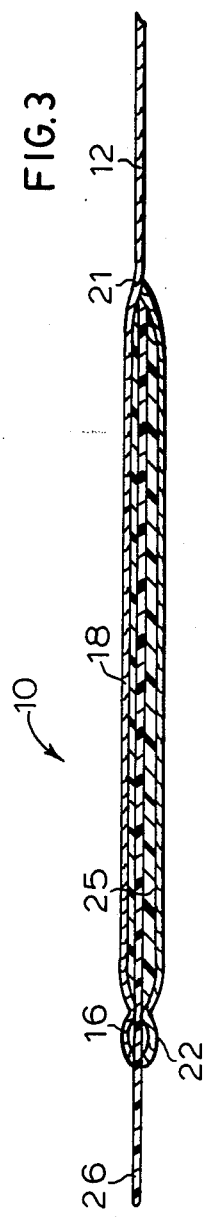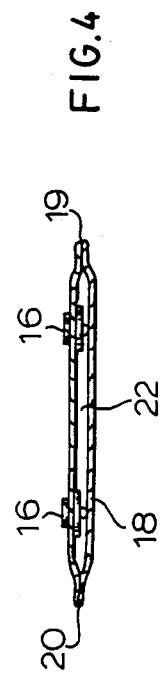

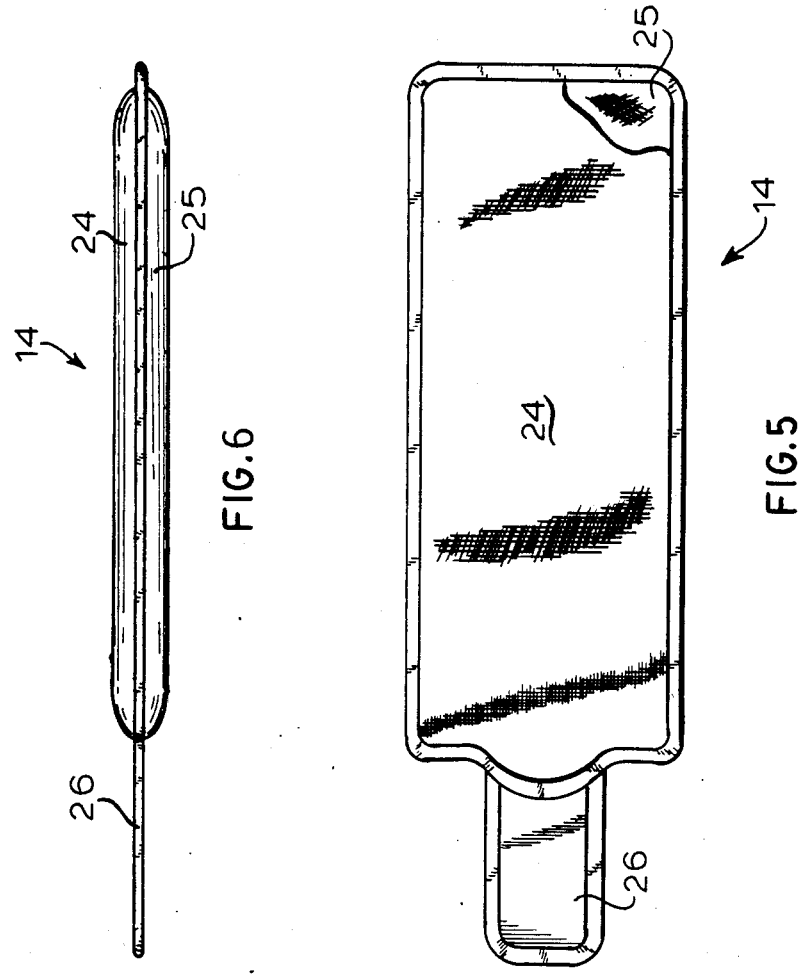

COLD APPLICATION AND COMPRESSIVE BANDAGE

BACKGROUND OF THE INVENTION

1. Field of the Invention

The present invention relates to an elastic bandage, and more particularly, concerns an elastic bandage for the simultaneous application of cold therapy and compression during use. 2. Description of the Prior Art Cold therapy is oftentimes recommended, particularly when a limb of a person has been injured. In many instances merely holding an ice bag against the injured portion may be sufficient. On the other hand, the mere manual application of an ice bag to the injury does not include the therapeutic benefits of compression. Furthermore, holding the ice bag in place by hand is inconvenient.

A therapeutic elastic bandage described in U.S. Pat. No. 3,900,035 represents a recent attempt to overcome the deficiencies of manual ice bag application. Since the patented product uses an elastic bandage, the benefits of compression, along with cold therapy application, are said to be achieved. However, some problems still exist in the type of bandage described in U.S. Pat. No. 3,900,035. In particular, in applying the bandage to the person's limb, the cold pack area would have to be grasped. If the wrap is difficult to complete, holding the cold pack area for a long period of time might induce some discomfiture. Also, in the patented bandage, insertion and removal of the multiple cold packs is time consuming. Further, in applying the bandage described in the aforementioned patent, the stretch of the elastic material increases the spacing between the individual cold packs thereby creating a discontinuous cold application surface. Therefore, it can be seen that further improvements in this type of therapeutic elastic bandage are still being sought.

U.S. Pat. No. 3,822,705 describes a refrigerant wrap which could be applied under compression to the area of injury. However, this patent suffers from the same deficiencies as the bandage described in the previously discussed patent.

SUMMARY OF THE INVENTION

The bandage of the present invention is adapted for simultaneous application of cold therapy and compression, particularly to a portion of a user's body. The bandage comprises an elastic material for wrapping around a portion of the body. A refrigeratable pack includes tab means thereon. The refrigeratable pack is removably held on said material during use so that the tab means is accessible for grasping by the user.

In a preferred embodiment of the present invention, the bandage includes an elongated strip of elastic material. There is a pocket in one end of the strip with an opening at the terminal end thereof. A flexible refrigeratable pack is removably placed inside the pocket, with the pack including a tab projecting outwardly through the opening. At least two operable fasteners are on the terminal end of the strip spaced sufficiently apart from each other to allow the tab to project therebetween when the fasteners are closed and to retain the pack inside the pocket during use.

In accordance with the principles of the present invention, the tab provides a convenient grasping mechanism for the user particularly during wrapping of the bandage around a portion of the body. In addition to allowing the user a facilitated mechanism for wrapping, the present invention also eliminates the need for the user to actually grasp the cold area of the bandage during the wrapping procedure. In addition, by placing the grasping tab on the refrigeratable pack, and not on the bandage, the unwieldy attachment problems are solved. Furthermore, it facilitates the fabrication of the present invention, from the standpoint of expense and equipment, to place the grasping tab on the refrigeratable pack rather than on the bandage. This becomes especially evident when the refrigeratable pack is required to be removed from the bandage after its coolth dissipates during use. The grasping tab allows the user to readily pull the refrigeratable pack out of the bandage without having to fumble with the refrigeratable pack if no tab were included. Another advantage is gained by having the grasping tab on the cold pack: by holding the tab, the user prevents any possible migration of the cold pack within the bandage pocket. Of course, the present invention desirably provides for the simultaneous application of cold therapy and compression during its use.

BRIEF DESCRIPTION OF THE DRAWINGS

FIG. 2 is a top plan view of the pouch portion of the bandage of FIG. 1 illustrating the insertion or removal of the refrigerant pack therefrom;

FIG. 3 is a cross-sectional view of the invention taken along line 3—3 of FIG. 1;

FIG. 4 is a cross-sectional view of the invention taken along line 4—4 of FIG. 1;

FIG. 5 is a top plan view of the preferred refrigerant pack of the present invention;

FIG. 6 is a side view of the refrigerant pack of FIG. 5; and

DETAILED DESCRIPTION

Figure 1:
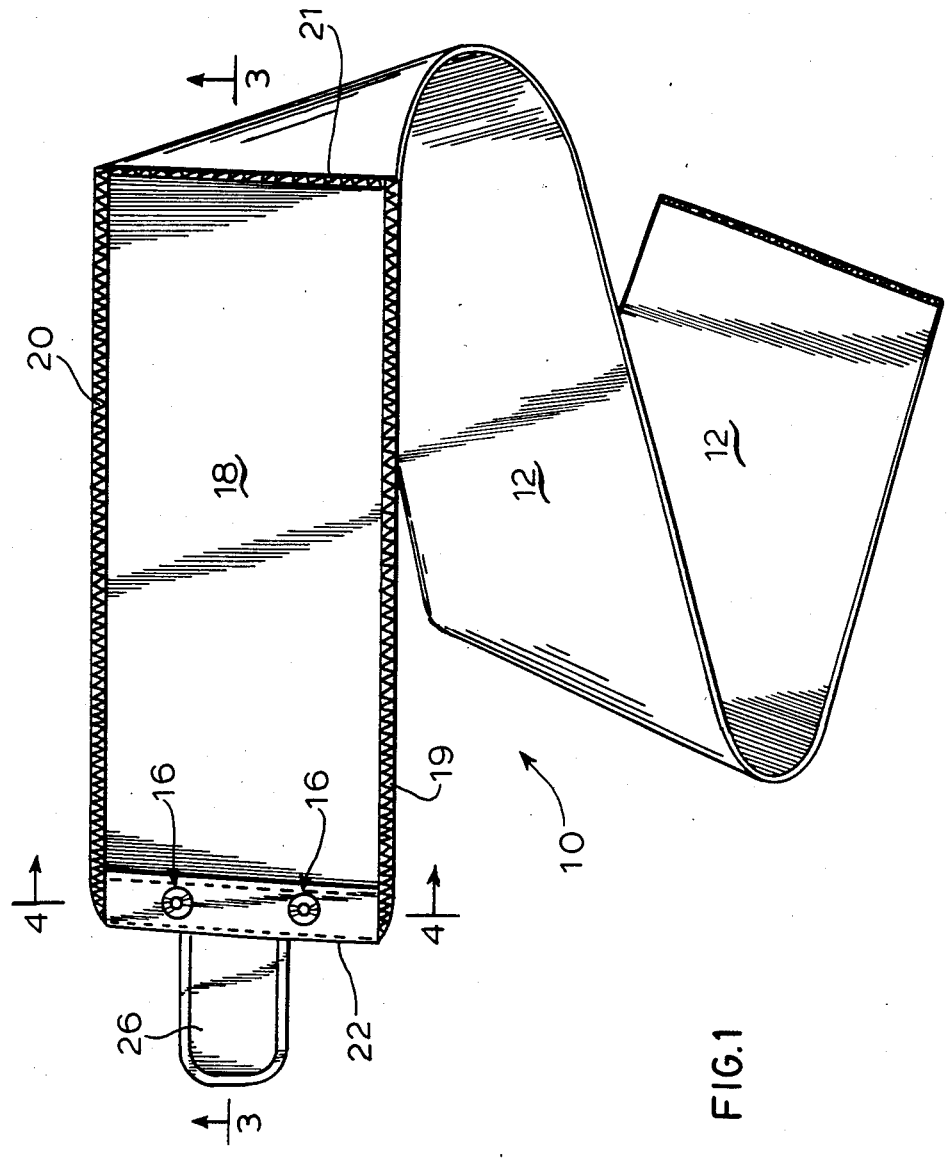
FIG. 1 is a perspective view illustrating the preferred embodiment of the bandage of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIGS. 1-4 in particular, there is illustrated the preferred embodiment of the bandage 10 of the present invention. Bandage 10 is comprised of three major components: a preferably elongated strip of elastic material 12, a removable refrigeratable pack 14 and a fastener assembly 16 for retaining the pack inside the pocket during use and for allowing the pack to be removed when necessary.

Elastic strip 12 is preferably significantly longer in its longitudinal dimension than its width so that it may be properly wrapped around a portion of the user's body. Typically, in its relaxed condition, the elastic strip of material may be about 36 inches (90 cm.) long by about 6 inches (15 cm.) wide. Of course, these dimensions are merely for illustration only and can be varied. The elastic strip of material is preferably fabricated with elastic stretch yarns which are interwoven into the material. One such material which may be used for the present invention is the ACE ® brand elastic bandage (ACE is a registered trademark of Becton, Dickinson and Company, Paramus, New Jersey).

At one end of strip 12 a pocket 18 is formed. One convenient manner to form pocket 18 is to overlay the strip 12 with a shorter piece of similar material and sew the two pieces of material together. This embodiment is illustrated in the drawings wherein three sides of the overlying material are sewn along edges 19, 20 and 21, respectively. The fourth edge, at the terminal end of strip 12 is left unsewn so that it forms an opening 22 at such terminal end. Opening 22 thus provides access to the interior of pocket 18. In forming pocket 18, while it is preferable to employ elastic material for compatibility with the strip of elastic material, it is not essential for the functioning of the present invention. It is also to be understood that the pocket itself is merely a preferred embodiment since the refrigeratable pack need not be completely enclosed when it is wrapped around the portion of the user's body. However, complete enclosure, except for the projecting tab, presents a neater appearance while also serving to absorb any moisture, caused by condensation, which may appear on the exterior of the refrigeratable pack during use. Inasmuch as the refrigeratable pack itself should have a large surface area, it is preferred that pocket 18 also be somewhat elongated so as to be longer in its longitudinal dimension than its width dimension.

With reference to refrigeratable pack 14, FIGS. 5 and 6 illustrate the configuration of the preferred embodiment of such refrigeratable pack. This pack includes a body portion 24 which is typically a sealed, flexible enclosure for the refrigeratable material 25 inside. Refrigerant pack 14 is typical to those packs described in U.S. Pat. Nos. 3,780,537 and 3,885,403. Generally speaking, the enclosure for the refrigeratable pack may be a rugged but flexible plastic material; the refrigeratable material may be propylene glycol or any other material which is commonly known to serve as a freezing point depressant. It is desirable that both the refrigeratable material and the enclosure material for the refrigeratable pack remain flexible even at cold temperatures. To this end, the refrigeratable material should maintain a soft, gel-like consistency over a temperature range of about $-20°$ C. to $+21°$ C.

With respect to the size of refrigeratable pack 14, it is preferred that there be as large a surface area as is compatible with wrapping around a limb of a person. Both refrigeratable pack 14 and pocket 18 should be sized so that the refrigeratable pack can be inserted into the pocket through opening 22, and preferably be completely enclosed by the pocket, except for the projecting tab.

As illustrated in the drawings, there is an extension tab 26 projecting from one end of the refrigeratable pack. Tab 26 is preferably positioned so that it extends along the longitudinal axis of the refrigeratable pack, as more clearly seen by referring to FIG. 5. Furthermore, and especially when enclosure 24 of the refrigeratable pack is a plastic material, extension tab 26 may be integrally formed with enclosure 24 during its fabrication. Of course, if it is not so integrally formed, extension tab 26 may be secured to the refrigeratable pack by adhesives, melting operations, or other suitable attachment mechanisms.

In preparation for use refrigeratable pack 14 is placed inside pocket 18 so that extension tab 26 projects outwardly through opening 22 as more clearly seen in FIG. 1. Although pocket 18 completely encloses the refrigeratable pack once it is placed inside, a retention mechanism is provided with respect to opening 22 so that the refrigeratable pack cannot be pulled out of the pocket when the extension tab is grasped by the user during the wrapping procedure. In the embodiment being described, and as more clearly seen by referring to FIGS. 1, 2 and 4, a pair of snap fasteners 16 is provided at opening 22. These snap fasteners allow the opening 22 to be readily opened and closed for repeated usage. The snap fasteners are spaced sufficiently apart from each other so that extension tab 26 projects therebetween when the fasteners are closed. When the refrigeratable pack is inside the pocket and the snap fasteners are closed, pulling on the extension tab will cause the shoulder portions 28 of the refrigeratable pack (as seen in FIG. 2) to come in contact with the snap fasteners. This serves as an abutment stop to prevent the refrigeratable pack from being pulled out of the pocket by the normal grasping of the extension tab during use of this invention. It is appreciated that the snap fasteners can be opened to allow the refrigeratable pack to be removed for re-freezing or for the insertion of a different refrigeratable pack. It is also appreciated that the snap fasteners as described with the embodiment herein are merely one choice of a retention mechanism for holding the refrigeratable pack in proper position. Other fastening means may also be employed such as, but not limited to, zippers, safety-pins, clamps, VELCRO fasteners and the like. These fasteners should be operable so as to be readily opened and closed by the user with little or no inconvenience. There should preferably be a fastener associated with opening 22 so that an effective abutment stop is provided on each side of tab 26 in shoulder regions 28 of the refrigeratable pack. However, it is appreciated that a single fastener on only one side of the tab would be sufficient to hold the refrigeratable pack in place during use.

Figure 7:
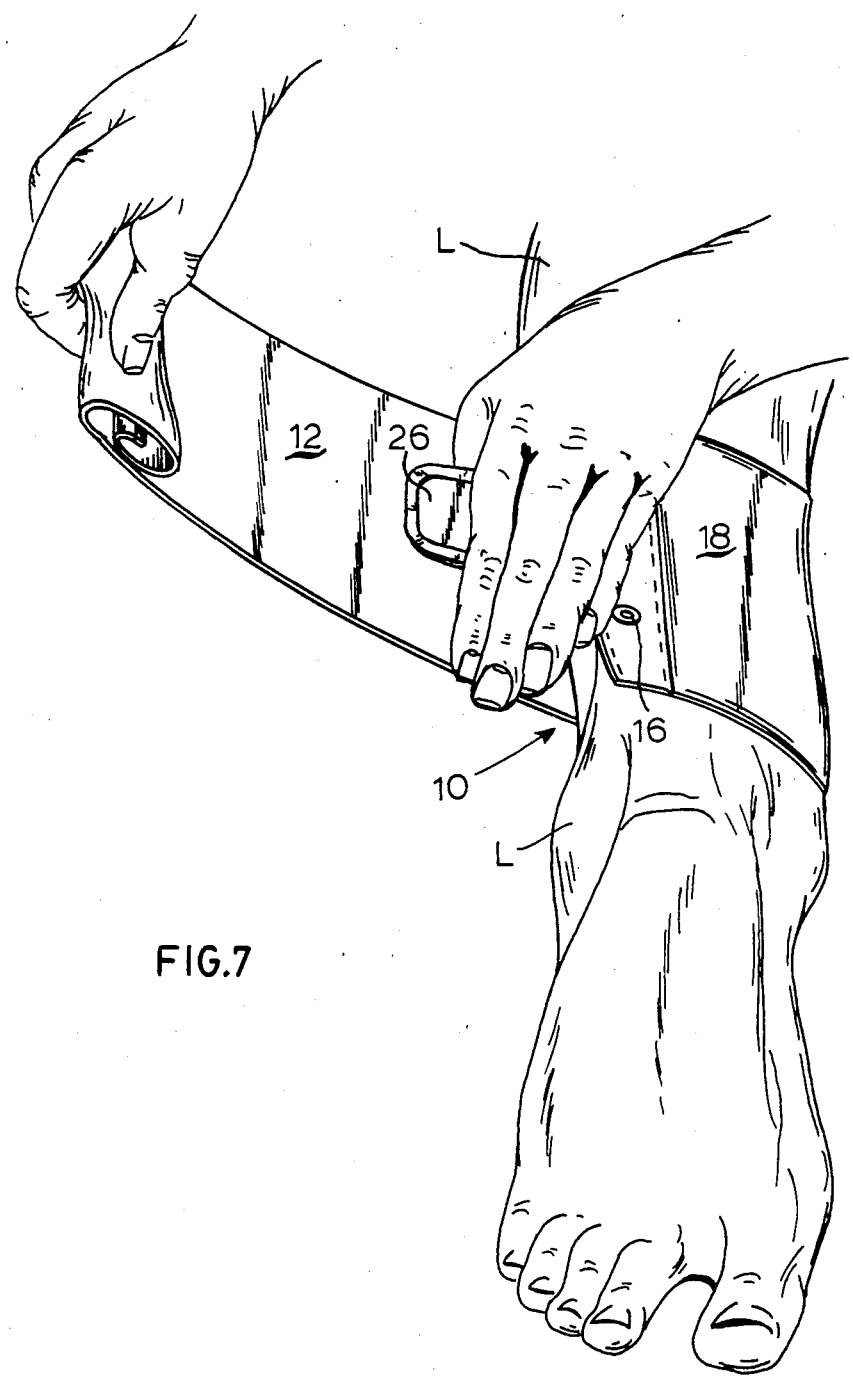
FIG. 7 is a perspective view of the bandage of FIG. 1 during the wrapping procedure around a limb of a user.

Turning now to FIG. 7, bandage 10 is illustrated during the wrapping procedure around a portion of a user's leg L. It can be seen that the user grasps extension tab 26 as he is positioning the bandage in position on a portion of leg L. Bandage 10 includes a cold refrigeratable pack inside pocket 18 for purposes of cold therapy and compression. While holding extension tab 26, the cold pack region of bandage 10 is applied first to the area of injury on leg L. Elongated strip of elastic material 12 is then stretched and wrapped around leg L and over the refrigeratable pack region. Usually, elongated strip 12 has sufficient original length and stretch to be wrapped a number of times around the leg. Various clamps, pins, fasteners and the like may then be employed to secure the bandage in position after wrapping is complete. The bandage then remains in place while delivering both cold therapy and compression to the site of wrap. Under normal conditions, the refrigeratable pack will retain its cold temperatures for approximately thirty minutes. When the refrigeratable pack is no longer cold, the elastic bandage is removed from the body portion being treated. Thereafter, the refrigeratable pack would be removed from the pocket of the bandage and then returned to the freezer for subsequent refrigeration. Of course, the bandage of the present invention can then be re-used repeatedly in this manner.

As illustrated in FIG. 7, the extension tab not only allows the user to positively grasp the end of the bandage for wrapping, but also keeps the user's hand off the cold area of the bandage during the wrapping procedure. Thus, the present invention provides a bandage for the simultaneous application of cold therapy and compression which is easily wrapped around a body portion of the user in a fashion which is more convenient than previously known therapeutic cold bandages.

What is claimed is:

1. A bandage for the simultaneous application of cold therapy and compression comprising:
   an elongated strip of elastic material adapted to be wrapped around a portion of a user's body;
   a pocket in one end of said strip with an opening at the terminal end of said strip providing access to the interior of the pocket;
   a refrigeratable pack removably placed inside said pocket, said pack including an extension tab projecting outwardly through said opening and adapted to be grasped by the user during wrapping of the bandage; and
   means for retaining said pack inside said pocket during use.

2. The bandage of claim 1 wherein said pack is made from flexible material.

3. The bandage of claim 2 wherein the pack has a refrigeratable material sealed therein which has a soft, gel-like consistency over a temperature range of about $-20°$ C. to $+21°$ C.

4. The bandage of claim 2 wherein said tab is integrally formed with said pack material.

5. The bandage of claim 1 wherein said means for retaining includes at least two fasteners on the terminal end of said strip spaced sufficiently apart from each other to allow said tab to project therebetween when said fasteners are closed.

6. The bandage of claim 5 wherein said fasteners are snap-type fasteners adapted to be readily opened and closed for repeated usage.

7. A bandage for the simultaneous application of cold therapy and compression comprising:
   an elongated strip of elastic material adapted to be wrapped around a portion of a user's body;
   an elongated pocket in one end of said strip with an opening at the terminal end of said strip;
   a refrigeratable pack adapted to be flexible over a temperature range of about $-20°$ C. to $+21°$ C. removably placed inside said pocket, said pack including an integrally formed tab projecting outwardly through said opening and adapted to be grasped by the user during wrapping of the bandage; and
   at least two operable fasteners on said terminal end of said strip spaced sufficiently apart from each other to allow said tab to project therebetween when said fasteners are closed and to retain said pack inside said pocket during use.

* * * * *